(12) United States Patent
Aberg et al.

(10) Patent No.: US 6,207,852 B1
(45) Date of Patent: Mar. 27, 2001

(54) SMOOTH MUSCLE SPASMOLYTIC AGENTS, COMPOSITIONS AND METHODS OF USE THEREOF

(75) Inventors: A. K. Gunnar Aberg, Sarasota, FL (US); George E. Wright; Jan L. Chen, both of Worcester, MA (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

(21) Appl. No.: 09/202,994

(22) PCT Filed: Jun. 30, 1997

(86) PCT No.: PCT/US97/11310

§ 371 Date: Dec. 23, 1998

§ 102(e) Date: Dec. 23, 1998

(87) PCT Pub. No.: WO98/00390

PCT Pub. Date: Jan. 8, 1998

Related U.S. Application Data

(60) Provisional application No. 60/021,012, filed on Jul. 1, 1996, provisional application No. 60/021,014, filed on Jul. 1, 1996, provisional application No. 60/021,015, filed on Jul. 1, 1996, and provisional application No. 60/021,028, filed on Jul. 1, 1996.

(51) Int. Cl.$^7$ .......................... C07C 69/76; C07C 233/00; C07C 49/23
(52) U.S. Cl. .............. 560/57; 564/171; 514/534; 514/617; 514/622; 568/329
(58) Field of Search .................... 514/622, 534, 514/617; 564/171; 560/57; 568/329

(56) References Cited

U.S. PATENT DOCUMENTS

| | | |
|---|---|---|
| 4,219,559 | 8/1980 | Janssens et al. ............ 424/267 |
| 4,835,161 | 5/1989 | Janssens et al. ............ 514/303 |
| 5,036,107 | 7/1991 | Rzeszotarski et al. . |
| 5,066,680 | 11/1991 | Shiokawa et al. . |
| 5,532,278 | 7/1996 | Aberg et al. . |

FOREIGN PATENT DOCUMENTS

| | | |
|---|---|---|
| 940540 | 7/1961 | (EP) . |
| 2222828 | * 3/1990 | (GB) . |

OTHER PUBLICATIONS

Database Chem. Abstr. (Columbus, OH, USA) Abstract No. 120:153730, Heuer, H. 'Synergistic Combinations of PAF antagonists and anticholinerigic agents as drugs for treatment of bronchial asthma', abstrct, DE 4219659 A1, Dec. 23, 1993.

Arch. int. Pharmacodyn., 1965, 156, No. 2 pp. 467–488; P.M. Lish et al.; "Oxybutynin—A Musculotropic Antispasmodic Drug with Moderate Anticholinergic Action".

The Journal of Pharm. and Experimental Therapeutics; vol. 256, No. 2; pp. 562–567; L. Noronha–Blob, et al.; "Enantiomers of Oxybutynin: In Vitro Pharmacological Characterization at M1,M2 and M3 Muscarinic Receptors and in Vivo Effects on Urinary Bladder Contraction, Mydriasis and Salivary Secretion in Guinea Pigs". (1991).

The Journal of Pharm. and Experimental Therapeutics; vol. 247, No. 3; pp. 867–872; Kachur, et al.; "R and S Enantiomers of Oxybutynin: Pharmacological Effects in Guinea Pig Bladder and Intestine" (1991).

The Journal of Urology; vol. 148, 595–597, Aug. 1992; Massad, et al.; "The Pharmacokinetics of Intravesical and Oral Oxygutynin Chloride".

Eur J. Clin Pharmacol (1988) 35: 515–520; Douchamps et al.; "The Pharmacokinetics of Oxybutynin in Man".

Drug Development Research 8:37–51 (1986); Meuldermans, et al.; "Excretion and Biotransformation of Astemizole in Rats, Guinea–Pigs, Dogs, and Man".

The Canadian Journal of Hospital Pharmacy—vol. 45, No. 1, Feb., 1992; pp. 33–37; "Astemizole and Terfenadine–Induced Cardiovascular Effects".

Arzneim–Forsch/Drug. Res. 41 (11), Nr. 9 (1991); Kamei, et al.; "Antiallergic Effects of Major Metabolites of Astemizole in Rats and Guinea Pigs".

Chem. Pharm. Bull. 40(6) 1415–1423 (1992); Take, et al.; "Agents for the Treatment of Overactive Detrusor. III. Synthesis and Structure–Activity Relationships of N–(4–Amino–2–butynyl)acetamide Derivatives".

J.Med. Chem. 1991, 34, 3065–3074; Carter et al.; "Analogues of Oxybutynin. Synthesis and Antimuscarinic and Bladder Activity of Some Substituted 7–Amino–1–hydroxy–5–heptyn–2–ones and Related Compounds".

Xenobiotica, 1992, vol. 22, No. 7, 859–869; Hughes, et al.; "Measurement of oxybutynin and its N–desethyl metabolite in plasma, and its application to pharmacokinetic studies in young, elderly and frail elderly volunteers."

Acta Pharmacol. et toxicol. 1984, 55–100–103; Aaltonen, et al.; "Antimuscarinic Activity of Oxybutynin in the Human Plasma Quantitated by a Radioreceptor Assay".

(List continued on next page.)

Primary Examiner—Paul J. Killos
(74) Attorney, Agent, or Firm—Nields & Lemack

(57) ABSTRACT

The present invention relates to smooth muscle spasmolytic agents, pharmaceutical compositions containing them and method of using said compounds and compositions for the treatment of urinary incontinence, gastric hyperactivity (ex. Irritable Bowel Syndrome) and other smooth muscle contractile conditions.

More particularly, the present invention relates to certain substituted esters, amides and ketones having smooth muscle relaxing properties while avoiding, on administration to a mammal, adverse side effects such as prominent antimuscarinic, arrhythmogenic and cardiodepressive effects.

26 Claims, No Drawings

OTHER PUBLICATIONS

Acta Pharm. Suec. 18, 25–34 (1981); Lindeke, et al.; "Determination of oxybutynin (4–diethylaminobut–2–ynyl 2–cyclohexyl–2–phenylglycolate) in serum and urine by gas chromatography/mass spectrometry with single ion detection".

Biomedical Mass Spectrometry, vol. 8, No. 10, 1981; pp. 506–513; "Metabolism of Oxybutnin: Establishment of Desethyloxybutynin and Oxybutynin N–Oxide Formation in Rat Liver Preparations Using Deuterium Substition and Gas Chromatographic Mass Spectrometric Analysis".

J.Med.Chem. 1991, 34, 3065–3074; Carter et al.; "Analogues of Oxybutynin. Synthesis and Antimuscarinic and Bladder Activity of Some Substituted 7–Amino–1–hydroxy–5–heptyn–2–ones and Related Compounds".

Chem.Pharm. Bull 40(6) 1415–1423 (1992); Take et al.; "Agents for the treatment of Overactive Detrusor.III. Synthesis and Structure–Activity Relationships of N–(4–Amino–2–butynyl)acetamide Derivatives".

Arch.int.Pharmacodyn., 1965, 156, No. 2; 467–488; Lish et al.; "Oxybutynin—A Musculotropic Antispasmodic Drug with Moderate Anticholinerigic Actions".

* cited by examiner

SMOOTH MUSCLE SPASMOLYTIC AGENTS, COMPOSITIONS AND METHODS OF USE THEREOF

This application claims priority from Provisional application Ser. Nos. Provisional Application No. 60/021,012 filed Jul. 1, 1996 Provisional Application No. 60/021,014 filed Jul. 1, 1996 Provisional Application No. 60/021,015 filed Jul. 1, 1996 Provisional Application No. 60/021,028 filed Jul. 1, 1996.

This application is a 371 of PCT/US97/11310 filed Jun. 30, 1997.

FIELD OF INVENTION

The present invention relates to smooth muscle spasmolytic agents, pharmaceutical compositions containing them and method of using said compounds and compositions for the treatment of urinary incontinence, gastric hyperactivity (ex. Irritable Bowel Syndrome) and other smooth muscle contractile conditions.

More particularly, the present invention relates to certain substituted esters, amides and ketones having smooth muscle relaxing properties while avoiding, on administration to a mammal, adverse side effects such as prominent antimuscarinic, arrhythmogenic and cardiodepressive effects.

REPORTED DEVELOPMENT

Racemic oxybutynin (OXY) is the leading drug for urinary incontinence and is also being used for the treatment in intestinal disorders, such as Irritable Bowel Syndrome (IBS). OXY is specifically used in the treatment of urinary urge incontinence. Urge incontinence is believed to be due to instability of the smooth muscle of the bladder (detrusor muscle). OXY exerts a direct antispasmodic effect on various forms of smooth muscle, mainly by inhibiting the action of acetylcholine on smooth muscle (anticholinergic activity). OXY is selective for muscarinic (acetylcholine) receptors over nicotinic (acetylcholine) receptors and as a result, no blocking effects are observed at skeletal neuromuscular junctions.

OXY relaxes urinary bladder smooth muscle and in patients with conditions characterized by involuntary bladder contractions, cystometric studies have demonstrated that OXY increases vesicle capacity, diminishes the frequency of involuntary contractions of the detrusor muscle, and delays the initial desire to void. There may be different reasons for urinary urge incontinence between patients. Thus involuntary bladder contractions may be caused by cholinergic or non-cholinergic mechanisms. The efficacy of OXY in the bladder has been attributed to a combination of antimuscarinic, direct spasmolytic and local anesthetic effects on the detrusor muscle. The racemic drug causes side effects such as drowsiness, impotence, diarrhea, mydriasis (dilated pupils), xerostomia (dry mouth) and tachycardia (fast heart beats). In fact, at least one researcher has referred to the "inevitable symptoms of mydriasis, xerostomia, tachycardia, etc." that accompany the administration of racemic oxybutynin (Lish et al. Arch. Int. Pharmacodyn. 156, 467–488 (1965), 481). Since cholinergic mechanisms are involved in the memory functions of the brain and the control of heart rate, anticholinergic drugs may be contraindicated in many patients, particularly in older patients. Other, clinically less serious anticholinergic side effects of oxybutynin are dry mouth (xerostomia), mydriasis and blurry vision. The high incidence of anticholinergic side effects by oxybutynin among patients with urinary incontinence, often results in reduction of the dosage or discontinuation of the therapy. Oxybutynin was originally developed as a membrane stabilizer (local anesthetic) and has therefore cardiac depressive effects that may limit its use in the elderly or in patients with cardiac disorders. In racemic oxybutynin, the cardiac depressive effects of the molecule are partly counteracted by the cardiac anticholinergic activity of the R-isomer, while that is not the case when the single S-isomer of oxybutynin is used for therapeutic purposes.

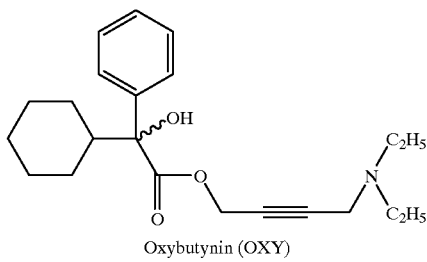

Oxybutynin (OXY)

Previous pharmacological studies of the individual enantiomers of OXY have suggested that the R-enantiomer is the therapeutically active enantiomer. Thus, Noronha-Blob et al. (J. Pharmacol. Exp. Ther. 256, 562–567 (1991)) concluded that the cholinergic antagonism of racemic oxybutynin (measured in vitro by its affinity for muscarinic receptor subtypes and in vivo for diverse physiological responses) could be attributed mainly to the activity of the R-enantiomer. For all muscarinic responses they found the rank order of potency of racemic oxybutynin and its enantiomers to be: (R)-oxybutynin (R-OXY) greater or equal to OXY, which was much greater than (S)-oxybutynin (S-OXY), with S-OXY being 1 to 2 orders of magnitude less potent than R-OXY as an antimuscarinic agent.

The S-isomer of oxybutynin has been suggested as a drug for urge incontinence (Aberg et al. U.S. Pat. No. 5,532,274). The present invention is concerned with compounds that have significantly less membrane stabilizing (cardiac depressant) activity than S-OXY (see above) and compounds that also have longer duration than S-OXY. The S-isomers of the compounds of the present invention are useful in the treatment of such types of urinary incontinence and other spasmogenic malfunctions, such as for example dysmenorrhea and certain types of irritable bowel syndrome, that are not caused by muscarinic mechanisms, while avoiding the side effects that reside in the corresponding R-isomers.

The R-isomers of the compounds of the present invention will be useful in the treatment of such types of urinary incontinence and other spasmogenic malfunctions that are caused by muscarinic mechanisms, while avoiding the side effects that reside in the corresponding S-isomers.

SUMMARY OF THE INVENTION

It has now been found that compounds with certain substituents (Table I) on the nitrogen atom of oxybutynin, have anticholinergic and/or calcium antagonistic activities, superior to those of oxybutynin. It has also been found that in certain cases, the (S)-isomers of said compounds have calcium antagonistic activities that are similar to the corresponding racemates and (R)-isomers. Most of the anticholinergic activity resides in the (R)-isomers of these compounds and the (S)-isomers have significantly less antimuscarinic activity than both the (R)-isomers and the racemates. Thus, practically all of the anti-cholinergic side effects of the racemic compounds (tachycardia, memory impairment, dry mouth, blurry vision etc.) reside in the (R)-isomer. However, the side effect of membrane stabilization that causes cardiac depressant effects in vivo, resides in both the (R)- and the (S)-isomers of these compounds. It has now been found that certain molecules have less membrane stabilizing activity and have therefore less cardiodepressant effects than OXY or S-OXY. Molecules have also been found that offer significantly longer durations of action in vivo than OXY or S-OXY, while the beneficial ratio between calcium antagonistic activity and anticholinergic activities, seen in S-OXY, were surprisingly well maintained, or even improved. Thus, the S-isomers of certain amides and ketones of the present invention offered less anticholinergic side effects than OXY and R-OXY, less cardiodepressive side effects than OXY, R-OXY and S-OXY and longer duration of activity than OXY, R-OXY and S-OXY.

It has now been found the optically pure (S)-4-dimethylamino-2-butyn-1-yl cyclohexylphenylglycolate, herein also called S-dimethyloxybutynin (S-DIMEO), provides medical treatment for urinary incontinence, while avoiding the strong anticholinergic side effects of racemic 4-dimethyl-amino-2-butyn-1-yl cyclohexyl-phenylglycolate, herein also called dimethyloxybutynin (DIMEO) and of (R)-4-dimethyl-amino-2-butyn-1-yl cyclohexylphenylglycolate, herein also called R-dimethyloxybutynin (R-DIMEO). Furthermore, analogs to S-DIMEO where the ester bridge was replaced by an amide (Examples 4 and 5) or an keto link (Examples 6 and 7), offered a longer duration of activity, while still avoiding the anticholinergic and the membrane stabilizing side effects, mentioned above.

S-DIMEO and the aforementioned S-DIMEO analogs are particularly useful in patients where urinary incontinence is caused by non-cholinergic mechanisms, which is believed to be the majority of all patients suffering from urinary urge incontinence. Compounds of this type are also useful for the treatment of various other spasmodic conditions, such as for example dysmenorrhea and certain types of irritable bowel syndrome. Non-cholinergic mechanisms causing irregular contractions of smooth muscles, include but are not limited to scars (i.e. from childbirth or surgical interventions), release of non-muscarinic neurotransmitters, platelet activating factor, leukotrienes, thromboxane or other non-muscarinic spasmogens, as well as other non-muscarinic mechanisms that cause a release of calcium ions into the cytosol of smooth muscle cells from intracellular or extracellular sources. The compounds of the invention offer calcium antagonistic activity without causing the side effect of lowering normal blood pressure.

Optically pure (R)-isomers and the racemates of said compounds, ex. dimethyloxybutynin (R-DIMEO and DIMEO) provide medical treatment in patients with urinary incontinence that primarily arise from cholinergic mechanisms; the single R-isomer being preferred in such cases since administration of the pure R-isomer avoids the side effects residing in the corresponding S-isomer.

Racemic oxybutynin is 4-(diethylamino)-2-butyn-1-yl cyclohexyl-phenylglycolate and hereinafter referred to as OXY. The generic name given to the hydrochloride salt of racemic oxybutynin by the USAN Council is oxybutynin chloride; it is sold under the name of Ditropan®. The preparation of racemic oxybutynin is described in Brit. Pat Spec. 940,540, the disclosure of which is hereby incorporated by reference.

The S-enantiomer of oxybutynin has the chemical name (S)-4-(diethylamino)-2-butyn-1-yl cyclohexylphenylglycolate and is hereinafter referred to as S-OXY and is described in U.S. Pat. No. 5,532,278, the disclosure of which is hereby incorporated by reference.

The R-enantiomer of oxybutynin has the chemical name (R)-4-(diethylamino)-2-butyn-1-yl cyclohexylphenylglycolate and is hereinafter referred to as R-OXY.

In accordance with the present invention, compounds having smooth muscle spasmolytic activity are provided comprising the following formulas:

Ester compounds represented by the formula:

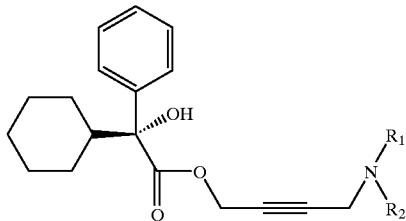

including possible stereochemically isomeric forms thereof and pharmaceutically acceptable salts thereof, wherein:
$R_1$ and $R_2$ are independently selected from the group consisting of: H, $CH_3$, $C_2H_5$, $C_3H_7$, $C_4H_9$, $(CH_2)_2OH$ and $(CH_2)_3OH$.

The overall process for preparing these esters is shown in Scheme III.

Amide compounds represented by the formula:

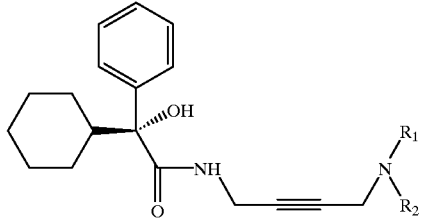

including possible stereochemically isomeric forms thereof and pharmaceutically acceptable salts thereof, wherein:
$R_1$ and $R_2$ are independently selected from the group consisting of: H, $CH_3$, $C_2H_5$, $C_3H_7$, $C_4H_9$, $(CH_2)_2OH$ and $(CH_2)_3OH$.

The overall process for preparing these amides is shown in Scheme IV.

Keto compounds represented by the formula:

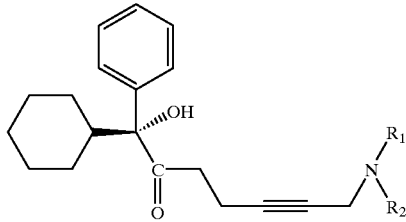

including possible stereochemically isomeric forms thereof and pharmaceutically acceptable salts thereof, wherein:
$R_1$ and $R_2$ are independently selected from the group consisting of: H, $CH_3$, $C_2H_5$, $C_3H_7$, $C_4H_9$, $(CH_2)_2OH$ and $(CH_2)_3OH$. The overall process for preparing these ketones is shown in Scheme V.

In another aspect, the present invention provides compounds having spasmolytic activity in a pharmaceutically acceptable vehicle.

In still another aspect, the present invention provides a method for the prevention of spasmogenic conditions in a mammal predisposed to such diseases and the treatment of smooth muscle spasmogenic diseases by administering at least one spasmolytic compound, or a pharmaceutical composition containing at least one spasmolytic compound to a mammal in need of such treatment. Spasmogenic diseases include urinary incontinence, intestinal smooth muscle hyperactivity (including IBS), untimely or painful uterine contractility (tocolysis, dysmenorrhea), renal and bile duct hyperactivity and other hyperactive smooth muscle conditions.

DETAILED DESCRIPTION OF THE INVENTION

Compounds of the Invention

1. The compounds of the present invention are shown in Tables I–III.

TABLE 1

Ester containing compounds.

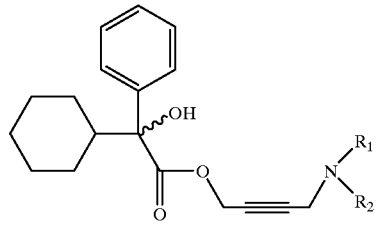

|   |   | $R_1$ | $R_2$ |
|---|---|---|---|
| (1) | 4-Amino-2-butyn-1-yl cyclohexyl-phenylglycolate | H | H |
| (2) | 4-(Methylamino)-2-butyn-1-yl cyclohexylphenylglycolate | H | $CH_3$ |
| (3) | 4-(Dimethylamino)-2-butyn-1-yl cyclohexylphenylglycolate | $CH_3$ | $CH_3$ |
| (4) | 4-(N-Methyl-N-ethylamino)-2-butyn-1-yl cyclohexylphenylglycolate | $CH_3$ | $C_2H_5$ |
| (5) | 4-(N-(2-Hydroxyethyl)amino)-2-butyn-1-yl-cyclohexylphenylglycolate | H | $(CH_2)_2OH$ |
| (6) | 4-(N-Methyl-N-(2-hydroxyethyl)amino)-2-butyn-1-yl cyclohexylphenylglycolate | $CH_3$ | $(CH_2)_2OH$ |
| (7) | 4-(N-Ethyl-N-(2-hydroxyethyl)amino)-2-butyn-1-yl cyclohexylphenylglycolate | $C_2H_5$ | $(CH_2)_2OH$ |
| (8) | 4-(N,N-Di-(2-hydroxyethyl)amino)-2-butyn-1-yl cyclohexylphenylglycolate | $(CH_2)_2OH$ | $(CH_2)_2OH$ |
| (9) | 4-(N-(3-Hydroxypropyl)amino)-2-butyn-1-yl cyclohexylphenylglycolate | H | $(CH_2)_3OH$ |
| (10) | 4-(N-Methyl-N-(2-hydroxypropyl)amino)-2-butyn-1-yl cyclohexylphenylglycolate | $CH_3$ | $(CH_2)_3OH$ |
| (11) | 4-(N-Ethyl-N-(3-hydroxypropyl)amino)-2-butyn-1-yl cyclohexylphenylglycolate | $C_2H_5$ | $(CH_2)_3OH$ |
| (12) | 4-(N-(2-Hydroxyethyl)-N-(3-hydroxypropyl)amino)-2-butyn-1-yl cyclohexylphenylglycolate | $(CH_2)_2OH$ | $(CH_2)_3OH$ |
| (13) | 4-(N,N-Di-(3-hydroxypropyl)amino)-2-butyn-1-yl cyclohexylphenylglycolate | $(CH_2)_3OH$ | $(CH_2)_3OH$ |

TABLE II

Amide-containing compounds.

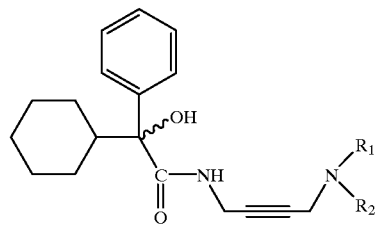

|   |   | $R_1$ | $R_2$ |
|---|---|---|---|
| (1) | N-(4-Amino-2-butyn-1-yl) cyclohexylphenyl-glycolamide | H | H |
| (2) | N-(4-(Methylamino)-2-butyn-1-yl) cyclohexyl-phenylglycolamide | H | $CH_3$ |
| (3) | N-(4-(Ethylamino)-2-butyn-1-yl) cyclohexyl-phenylglycolamide | H | $C_2H_5$ |
| (4) | N-(4-(Dimethylamino)-2-butyn-1-yl) cyclohexyl-phenylglycolamide | $CH_3$ | $CH_3$ |
| (5) | N-(4-(Diethylamino)-2-butyn-1-yl) cyclohexyl-phenylglycolamide | $C_2H_5$ | $C_2H_5$ |
| (6) | N-(4-(N'-Methyl-N'-ethylamino)-2-butyn-1-yl cyclohexyl-phenylglycolamide | $CH_3$ | $C_2H_5$ |

TABLE II-continued

Amide-containing compounds.

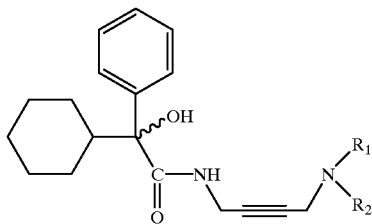

|  |  | R₁ | R₂ |
|---|---|---|---|
| (7) | N-{4-(N'-(2-Hydroxyethyl)amino)-2-butyn-1-yl} cyclohexyl-phenylglycolamide | H | (CH₂)₂OH |
| (8) | N-{4-(N'-Methyl-N'-(2-hydroxyethyl)amino)-2-butyn-1-yl} cyclohexylphenylglycolamide | CH₃ | (CH₂)₂OH |
| (9) | N-{4-(N'-Ethyl-N'-(2-hydroxyethyl)amino)-2-butyn-1-yl} cyclohexylphenylglycolamide | C₂H₅ | (CH₂)₂OH |
| (10) | N-{4-(N',N'-Di-(2-hydroxyethyl)amino)-2-butyn-1-yl cyclohexylphenylglycolamide | (CH₂)₂OH | (CH₂)₂OH |
| (11) | N-{4-(N-(3-Hydroxypropyl)amino)-2-butyn-1-yl} cyclohexylphenylglycolamide | H | (CH₂)₃OH |
| (12) | N-{4-(N'-Methyl-N'-(3-hydroxypropyl)amino)-2-butyn-1-yl} cyclohexylphenylglycolamide | CH₃ | (CH₂)₃OH |
| (13) | N-{4-(N'-Ethyl-N'-(3-hydroxypropyl)amino)-2-butyn-1-yl} cyclohexylphenylglycolamide | C₂H₅ | (CH₂)₃OH |
| (14) | N-{4-(N'-(2-Hydroxyethyl)-N'-(3-hydroxypropyl)amino)-2-butyn-1-yl} cyclohexylphenylglycolamide | (CH₂)₂OH | (CH₂)₃OH |
| (15) | N-{4-(N',N'-Di-(3-hydroxypropyl)amino)-2-butyn-1-yl} cyclohexylphenylglycolamide | (CH₂)₃OH | (CH₂)₃OH |

TABLE III

Keto-containing compounds.

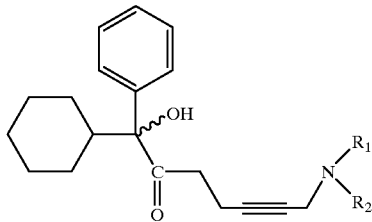

|  |  | R₁ | R₂ |
|---|---|---|---|
| (1) | 7-Amino-1-cyclohexyl-1-hydroxy-1-phenylhept-5-yn-2-one | H | H |
| (2) | 7-(Methylamino)-1-cyclohexyl-1-hydroxy-1-phenylhept-5-yn-2-one | H | CH₃ |
| (3) | 7-(Ethylamino)-1-cyclohexyl-1-hydroxy-1-phenylhept-5-yn-2-one | H | C₂H₅ |
| (4) | 7-(Dimethylamino)-1-cyclohexyl-1-hydroxy-1-phenylhept-5-yn-2-one | CH₃ | CH₃ |
| (5) | 7-(Diethylamino)-1-cyclohexyl-1-hydroxy-1-phenylhept-5-yn-2-one | C₂H₅ | C₂H₅ |
| (6) | 7-(N-Methyl-N-ethylamino)-1-cyclohexyl-1-hydroxy-1-phenylhept-5-yn-2-one | CH₃ | C₂H₅ |
| (7) | 7-(N-(2-Hydroxyethyl)amino)-1-cyclohexyl-1-hydroxy-1-phenylhept-5-yn-2-one | H | (CH₂)₂OH |
| (8) | 7-(N-Methyl-N-(2-hydroxyethyl)amino)-1-cyclohexyl-1-hydroxy-1-phenylhept-5-yn-2-one | CH₃ | (CH₂)₂OH |
| (9) | 7-(N-Ethyl-N-(2-hydroxyethyl)amino)-1-cyclohexyl-1-hydroxy-1-phenylhept-5-yn-2-one | C₂H₅ | (CH₂)₂OH |
| (10) | 7-(N,N-Di(2-hydroxyethyl)amino)-1-cyclohexyl-1-hydroxy-1-phenylhept-5-yn-2-one | (CH₂)₂OH | (CH₂)₂OH |
| (11) | 7-(N-(3-Hydroxypropyl)amino)-1-cyclohexyl-1-hydroxy-1-phenylhept-5-yn-2-one | H | (CH₂)₃OH |

TABLE III-continued

Keto-containing compounds.

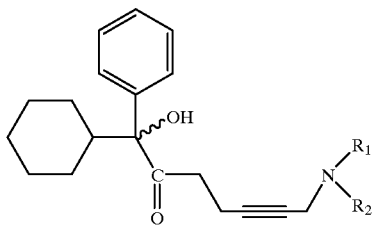

| | | $R_1$ | $R_2$ |
|---|---|---|---|
| (12) | 7-(N-Methyl-N-(2-hydroxypropyl)amino)-1-cyclohexyl-1-hydroxy-1-phenylhept-5-yn-2-one | $CH_3$ | $(CH_2)_3OH$ |
| (13) | 7-(N-Ethyl-N-(3-hydroxypropyl)amino)-1-cyclohexyl-1-hydroxy-1-phenylhept-5-yn-2-one | $C_2H_5$ | $(CH_2)_3OH$ |
| (14) | 7-(N-(2-Hydroxyethyl)-N-(3-hydroxypropyl)amino)-1-cyclohexyl-1-hydroxy-1-phenylhept-5-yn-2-one | $(CH_2)_2OH$ | $(CH_2)_3OH$ |
| (15) | 7-(N,N-Di-(3-hydroxypropyl)amino)-1-cyclohexyl-1-hydroxy-1-phenylhept-5-yn-2-one | $(CH_2)_3OH$ | $(CH_2)_3OH$ |

2. Syntheses of the compounds of the invention are shown in Schemes I–V.

Scheme I.
Synthesis and Resolution of Cyclohexylphenylglycolic Acid

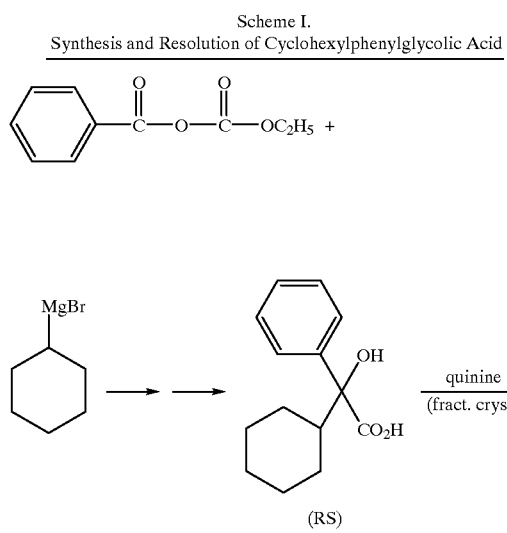

Scheme II.
Synthesis of Didesethyloxybutynin (DIDEO)

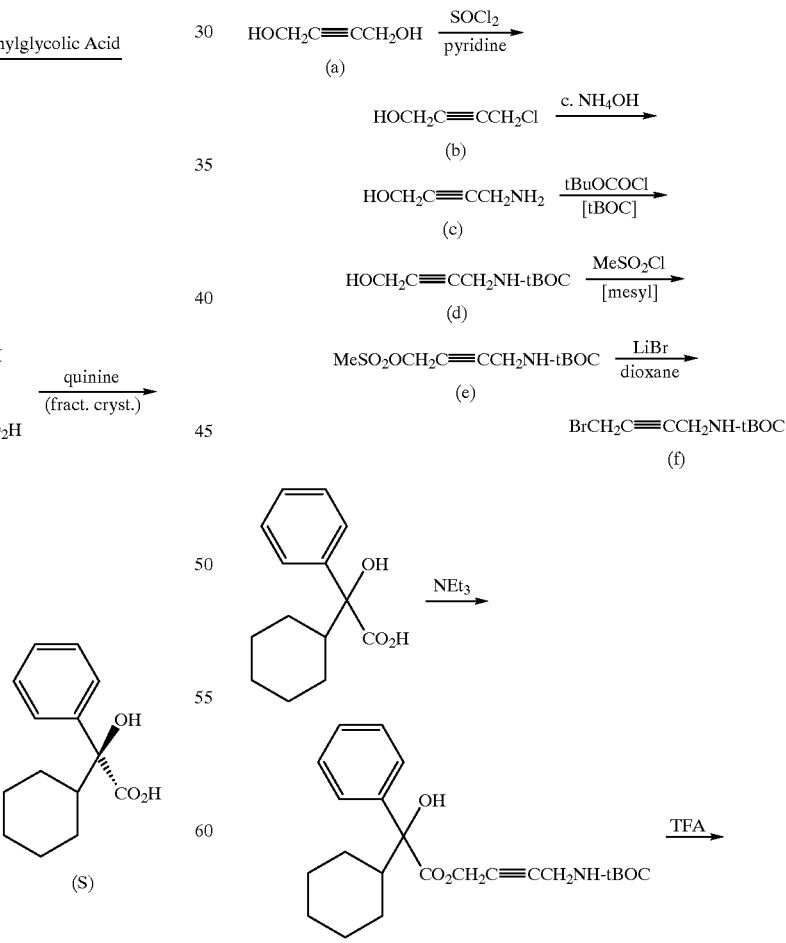

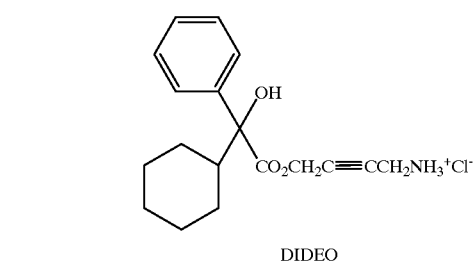
DIDEO
Scheme III.
Synthesis of Alkylamino and Hydroxyalkylamino Esters.
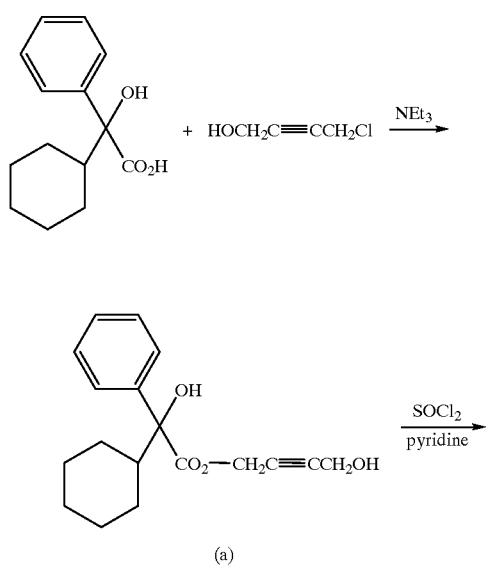
(a)
(b)
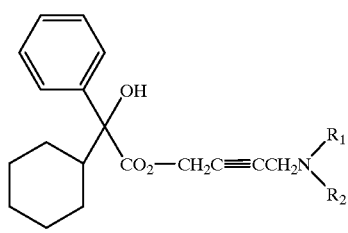
Scheme IV.
Synthesis of Amide-Containing Compounds.
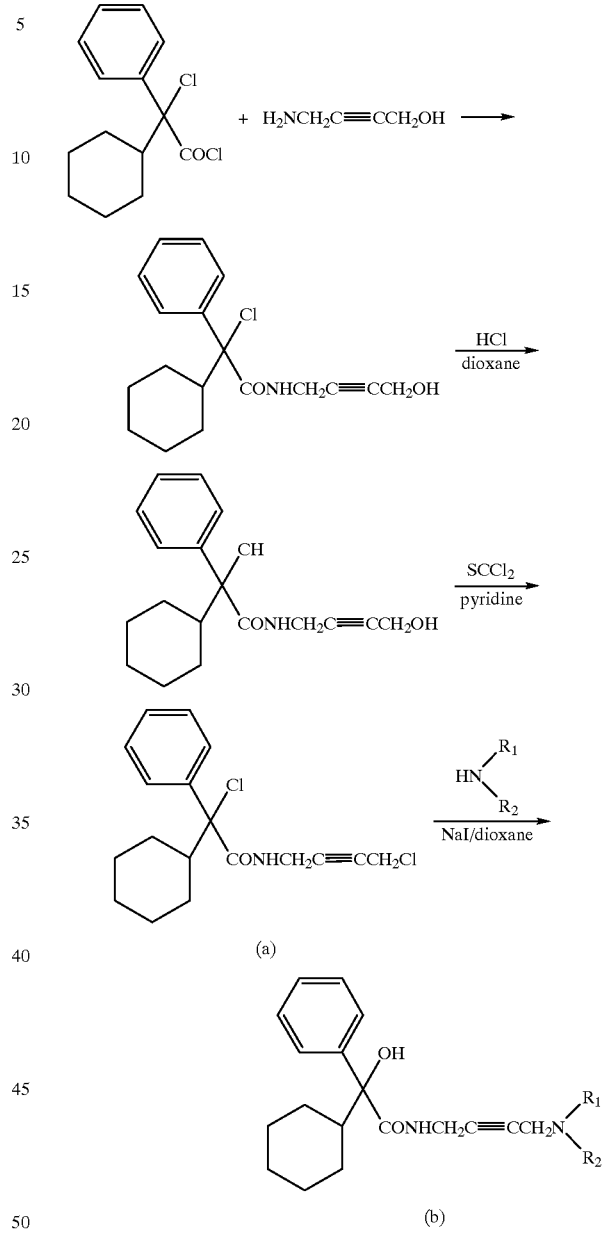
(a)
(b)
Scheme V.
Synthesis of Keto-Containing Compounds.
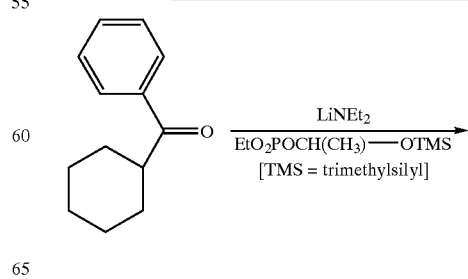

-continued

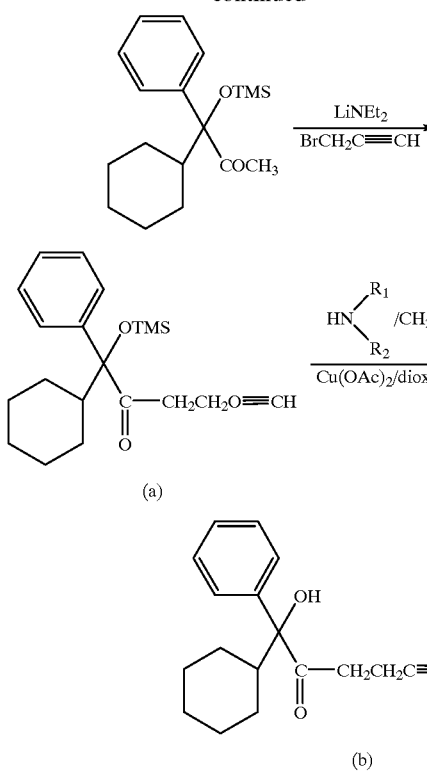

(a)

(b)

1. Ester-Containing Compounds.

(RS)-Cyclohexylphenylglycolic acid was synthesized according to Scheme I by addition of cyclohexyl magnesium bromide to ethyl benzoylformate, followed by alkaline hydrolysis (Hoffman and Schnellenberg, Helv. Chim. Acta 1947, 30: 292). The racemic acid was resolved by fractional crystallization as the quinine salt (Barlow et al. J. Med. Chem. 1973, 16: 439). Eight cycles of crystallization produced S-cyclohexylphenylglycolic acid and 98% enantiomeric excess (ee).

EXAMPLE 1

Utilizing appropriate starting materials, the compound having the formula

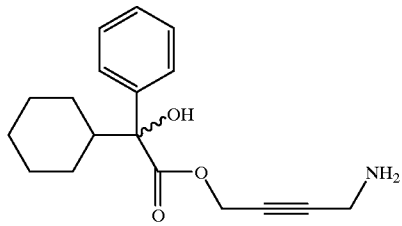

and the chemical name 4-amino-2-butyn-1-yl-cyclohexylphenyl-glycolate, herein also referred to at DIDEO, was prepared according to Scheme II. 2-Butyn-1, 4-diol (compound a) was selectively converted to the monochloro compound (b) and then to the aminoalkynol (c). The amino group was protected as the tert-butoxycarbonyl (t-BOC) derivative (d) and the hydroxyl group was activated as the mesyl derivative (e). Displacement of the mesyloxy group by bromo gave the final intermediate (f). Base-catalyzed displacement of the bromo group of (f) by cyclohexylphenyl-glycolic acid gave the desired t-BOC-protected ester in 89% yield. Deprotection with trifluoroacetic acid (TFA) gave the desired DIDEO, isolated as the hydrochloride. When the S-acid was used in the displacement step, S-DIDEO was obtained.

EXAMPLE 2

Utilizing appropriate starting materials, the compound having the formula

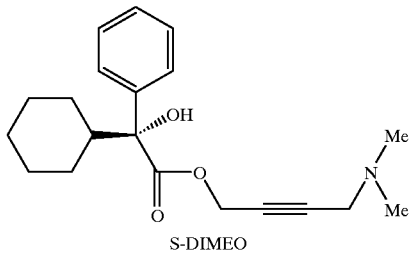

S-DIMEO and the chemical name 4-dimethylamino-2-butyn-1-yl cyclohexylphenyl-glycolate, herein also referred to at DIMEO, was prepared according to Scheme 3. Cyclohexylphenylglycolic acid is reacted with 4-chloro-2-butyn-1-ol, prepared as taught by Bailey and Fujiwara (J. Am. Chem. Soc. 1954, 77: 165), to give (a). Reaction of (a) with thionyl chloride gives the 4-chloro-2-butynyl ester, (b). Treatment of (b) with dimethylamine gives DIMEO. Use of the S-acid in the sequence gives S-DIMEO.

EXAMPLE 3

Utilizing appropriate starting materials, the compound having the formula

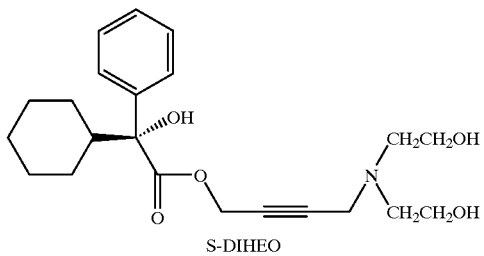

S-DIHEO and the chemical name (S)-4-dihydroxyethylamino-2-butynyl-cyclohexyl-phenyl-glycolate, herein also referred to at S-DIHEO, was also prepared according to Scheme III. Treatment of the 4-chloro-2-butynyl ester (b) with di(2-hydroxyethyl)amine gives DIHEO. Use of the S-acid in the sequence gives S-DIHEO.

2. Amide-Containing Compounds.

The general procedure in Scheme IV follows that developed for analogous compounds by Take et al (Chem. Pharm. Bull. 1992, 40:1415). In short, the 4-chloro-2-butynylamide analog (a) is treated with ammonia or the appropriate alkylamine or hydroxyalkylamine to give the desired compound (b). Because the synthesis begins with the racemic chloromandelic acid chloride, the final product can be resolved with D-tartaric acid, as taught by Take et al. (Chem. Pharm. Bull. 1992, 40:1415), to give the S-enantiomers.

EXAMPLE 4

Utilizing appropriate starting materials, the compound having the formula

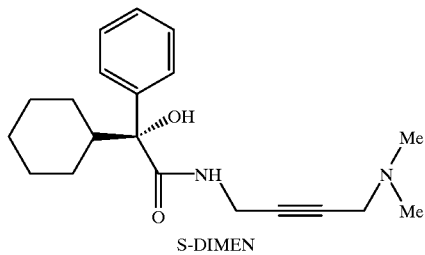

S-DIMEN and the chemical name N-(4-Dimethylamino)-2-butyn-1-yl) cyclohexyl-phenylglycolamide, herein also referred to as DIMEN, was prepared according to Scheme 4. The 4-chloro-2-butynylamide analog (a) was reacted with dimethylamine to give RS-DIMEN. The racemate was resolved by fractional crystallization with D-tartaric acid to give S-DIMEN in 98% enantiomeric excess.

EXAMPLE 5

Utilizing appropriate starting materials, the compound having the formula

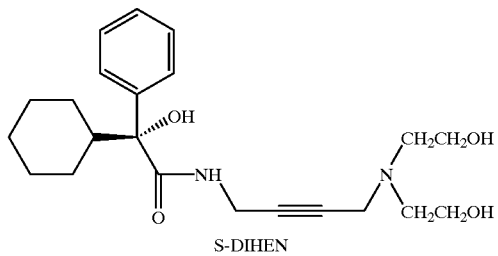

S-DIHEN and the chemical name N-{4-(N',N'-Di(2-hydroxyethyl)amino)-2-butyn-1-yl} cyclohexylglycolamide, herein also referred to as DIHEN, was also prepared according to Scheme 4. The 4-chloro-2-butynyl-amide analog (a) was reacted with di(2-hydroxyethyl)amine to give (RS)-DIHEN. The racemate was dissolved by fractional crystallization with D-tartaric acid to give S-DIHEN in 98% ee.

3. Keto-Containing Compounds.

The general procedure in Scheme V is used to prepare these compounds, as taught by Carter et al. (J. Med. Chem. 1991, 34: 3065). The intermediate propynyl methyl ketone (a) is aminomethylated with ammonia or the corresponding alkylamine or hydroxylamine and formaldehyde to give the desired compound (b). Resolution of the racemic product is done with D-tartaric acid. Alternatively, the trimethylsilyl-protected methyl ketone may be synthesized as the S enantiomer from S-cyclohexylphenylglycolic acid as taught by Carter et al. (J. Med. Chem. 1991, 34: 3065).

EXAMPLE 6

Utilizing appropriate starting materials, the compound having the formula

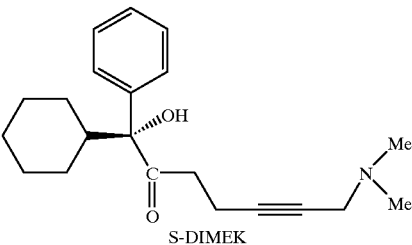

S-DIMEK and the chemical name 7-(dimethylamino)-1-cyclohexyl-1-hydroxy-1-phenylhept-5-yn-2-one, herein also referred to as DIMEK, was prepared according to Scheme V.

EXAMPLE 7

Utilizing appropriate starting materials, the compound having the formula

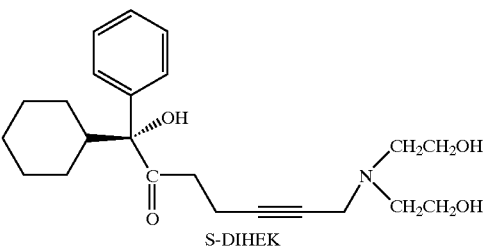

S-DIHEK and the chemical name 7-(N,N-Di(2-hydroxyethyl)amino)-1-cyclohexyl-1-hydroxy-1-phenylhept-5-yn-2-one, herein also referred to as DIHEK, was also prepared according to Scheme V.

Biological Testing

Compounds of the present invention are tested for the following effects utilizing art accepted methods referred hereunder:

A. Acute Toxicity in Mice.

The experiments are carried out on conscious albino mice that are administered intravenously or orally with escalating doses of the test compounds.

B. Ligand Binding Studies: Muscarinic Receptors.

The experiments are carried out on membranes prepared from SF9 cells infected with baculovirus to express muscarinic receptor subtypes. After incubation with the test article and the proper radioligand and washing, bound radioactivity is determined with a liquid scintillation counter, using a commercial scintillation cocktail. The specific radioligand binding to each receptor is defined as the difference between total binding and nonspecific binding determined in the presence of an excess of unlabelled ligand. $IC_{50}$ values (concentrations required to inhibit 59% of specific binding) are determined by non linear regression analysis of the competition curves. These parameters are obtained by curve fitting using Sigmaplot™ software.

C. Binding to Calcium Channels.
The assays are performed using the following methods:

| Receptors | Membranes | Reference Compounds | References |
|---|---|---|---|
| Ca channel (diltiazem site) | rat cerebral cortex | diltiazem | Schoemaker & Langer (1985) |
| Ca channel (verapamil site) | rat cerebral cortex | D600 | Reynolds et al (1986) |

The experimental conditions are:

| Receptors | Ligands | Conc. | Nonspecific | Incubation |
|---|---|---|---|---|
| Ca channel (diltiazem site) | $^3$H diltiazem | 5 nM | diltiazem (10 μM) | 120 min 25° C. |
| Ca channel (verapamil site) | $^3$H D888 | 0.5 nM | D 600 (10 μM) | 60 min 22° C. |

After incubation with the test article and the proper radioligand and washing, bound radioactivity is determined with by liquid scintillation, using a commercial scintillation cocktail. The specific radioligand binding to each receptor is defined as the difference between total binding and nonspecific binding in the presence of an excess of unlabelled ligand. $IC_{50}$ values (concentrations required to inhibit 59% of specific binding) are determined by non linear regression analysis of the competition curves. These parameters are obtained by curve fitting using Sigmaplot™ software.

D. Functional Characterization of Antimuscarinic/Antispasmodic Activity.

Bladder strips.

Experiments are performed using methods similar to those described by Kachur et al, 1988 and Noronha-Blob and Kachur, 1991. Strips of tissue (approximately 10 mm long and 1.5 mm wide) are removed from the body of the urinary bladder of male Hartley guinea pigs weighing 400–600 g. The tissues are suspended in an oxygenated buffer of the following composition, in mM: NaCl, 133; KCl, 4.7; $CaCl_2$, 2.5; $MgSO_4$, 0.6; $NaH_2PO_4$, 1.3; $NaHCO_3$, 16.3; and glucose, 7.7. They are maintained at 37.5 C. Contractions are recorded with isometric transducers (Model FT-10) on an ink-writing polygraph.

In each experiment up to seven strips are removed from a single bladder, suspended in individual tissue chambers and allowed to equilibrate with the bathing solution for one hour before proceeding with the experiment.

Carbachol-induced contractions.

One series of experiments focuses on the anticholinergic actions of the test compounds. In these experiments, in order to assess the viability of each tissue and to serve as a frame of reference, contractions of each strip of tissue are recorded initially in response to exposure to tissue medium in which the NaCl was replaced by KCl to yield a concentration of 137.7 mM KCl in the medium. This is followed by return to the standard medium, and then by exposures to progressively in creasing concentrations of carbachol, with separate exposures to each concentration only until the peak response has been recorded. Then, leaving one strip untreated and/or one strip exposed to the test solution to serve as control tissue(s), the remaining strips each are exposed for one hour to one concentration of an antagonist. Finally, the responses to increasing concentrations of carbachol followed by exposure to 137.7 mM KCl are recorded a second time.

Potassium-induced contractions.

A second series of experiments focuses on the functional calcium antagonistic effects of the substances being studied. Contractions are recorded in response to sequentially increasing the concentration of potassium in the medium.

Data analysis.

To determine whether antagonists decrease the peak response to agonists, the peak tension developed by each strip during the second set of determinations is expressed as a percent of the peak tension developed during the first concentration-effect determination. Then, for each antagonist the resultant data are analyzed for treatment-related differences by one-way analysis of variance (ANOVA). Since only one concentration of antagonist is studied in each strip of bladder, a modified procedure is used to estimate the pA2 and slope of the Schild regression. First, the concentrations of agonist producing a half-maximal response (the $EC_{50}$) is estimated for each strip from the second set of concentration-effect data. The $EC_{50}$ is obtained from linear regression lines fit to the logarithm of the concentration of drug and the responses bracketing the half maximum level of response. For each drug-treated strip, a "concentration ratio" (CR) is calculated as the ratio of the $EC_{50}$ of the treated tissue divided by the $EC_{50}$ of the untreated tissue. For each experiment where two or more strips are exposed to the same chemical but at different concentrations, the logarithm of this ratio minus one (i.e., log (CR-1)) is plotted against the logarithm of the concentration of antagonist to which the strip had been exposed to produce "Schild plots". A regression analysis relating log(CR-1) to the logarithm of the concentration of the antagonist is employed to estimate the pA2 and the slope of the regression line. Finally, experiments are grouped by chemical and the mean ±SEM of the pA2 and slope are calculated.

E. Cardiac Side Effects

Lengthening of the QT-interval of the EKG is a serious side effect of nonsedating antihistamines, since prolonged QT (or QTc) may cause a potentially lethal form of ventricular fibrillation, called Torsades de Pointes. One purpose of this study is to investigate whether the compounds of this invention cause prolongation of the cardiac action potential. This investigation also assesses the effects of the test compound on cardiac contractility and intra-cardiac conduction.

Male Hartley guinea pigs, weighing roughly 350–450 g, are used for this study. The guinea pigs are acclimatized under a 12-hr light-dark cycle for a one-week period prior to the tests. On the day of the study, the guinea pigs are injected with sodium heparin (1000 U/kg, IP). Fifteen min. later they are anesthetized with $CO_2$, after which the heart are rapidly excised and placed in a beaker of ice-cold saline until contraction ceases (usually within 30 sec). The isolated hearts are then mounted via the aortic root to cannulas and perfused retrogradely at a pressure of 88 mmHg with a physiological salt solution (PSS). The PSS is maintained at 37° C. and contains: 118 mM NaCl, 4.7 mM KCl, 2.25 mM $CaCl_2$, 1.18 mM $KH_2PO_4$, 1.17 mM $MgSO_4$, 25 mM $NaHCO_3$, and 11 mM dextrose. The PSS is aerated with 95% $O_2$/5% $CO_2$ to maintain pH at 7.4.

The hearts are paced at a rate of 225 bpm within a water-jacketed organ bath which is maintained at 37° C. Each heart is allowed to stabilize for 10–1 5 min., during which time a Millar pressure transducer is placed in the lumen of the left ventricle via a small incision in the left atrium. The Millar pressure transducer is used to measure left ventricular contractile function and heart rate.

The following measurements are made prior to and following treatment with each concentration of test compound, reference agent or vehicle.

left ventricular systolic, end-diastolic, and developed pressures

+dP/dt$_{max}$ and −dP/dt$_{max}$

QT-interval

QT$_c$, (QT-interval corrected for heart rate)

PR-interval

QRS-interval

Two to three measurements are made during the stabilization period. Once hemodynamic and electrocardiographic parameters have stabilized, a procedure similar to that previously described by Haleen et al. (1) is used to assess the direct effects of each test compound, on the isolated guinea pig heart. Increasing concentrations of the test compound are added to the perfusate at 10–15 min. intervals (depending on the time required to obtain a stable response). Measurements are repeated during the last one to two min. of the perfusion period for each concentration of the test compound.

The total time required for evaluating the response to each test compound, reference agent or vehicle does not exceed 120 min. Each treatment group contains three hearts.

Clinical Doses of Compounds of the Present Invention

The magnitude of a prophylactic or therapeutic dose of the compounds of this invention in the acute or chronic management of disease will vary with the severity and nature of the condition to be treated and the route of administration. The dose and the frequency of the dosing will also vary according to the age, body weight and response of the individual patient. In general, the total daily dose range for the compounds of this invention for the conditions described herein is from about 0.5 mg to about 100 mg in single or divided doses. The ester-containing compounds will preferably be given in divided doses. Compounds with amide or keto-groups in the molecule have longer biological half-lives than the corresponding esters and may therefore be given in fewer daily occasions than the esters. In managing the patient, the therapy can be initiated at a lower dose, perhaps at about 0.5 mg to about 25 mg, and may be increased up to about 200 mg depending on the patient's global response. It is further recommended that patients over 65 years and those with impaired renal or hepatic function initially receive low doses and that they be titrated based on individual response(s) and plasma drug level(s). It may be necessary to use dosages outside these ranges, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat incontinence but insufficient to cause adverse effects" are encompassed by the above-described dosage amounts and dose frequency schedule.

Routes of Administration of the Present Invention

Any suitable route of administration may be employed for providing the patient with an effective dosage of the compounds of this invention. For example, oral, sublingual, rectal, parental (subcutaneous, intramuscular, intravenous), transdermal, aerosol and like forms of administration may be employed. Additionally, solutions containing the drug may be administered directly into the bladder through the urethra. Dosage forms include tablets, troches, dispersions, suspensions, solutions, capsules, microencapsulated systems, transdermal delivery systems, and the like.

Pharmaceutical Compositions of the Present Invention

The pharmaceutical compositions of the present invention comprise at least one compound of the present invention as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids or bases. Examples of suitable pharmaceutically acceptable acid addition salts for the compounds of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. Examples of such bases include metallic salts made from aluminum, calcium, lithium, magnesium, potassium, sodium, and zinc, while appropriate organic bases may be selected, for example from N,N'-dibenzylethylenediamine, chloroprocaine, choline, diethanolamine, ethylenediamine, meglumaine (N-methylglucamine), lysine and procaine.

The compositions of the present invention include suspensions, solutions, elixirs, aerosols or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations for administration to adults, while oral liquid preparations may be preferred for administration to children.

Because of their ease of administration, tablets and capsules represent one of the more advantageous oral dosage unit forms, in which case solid pharmaceutical carriers are employed. If desired, tablets may be coated by standard aqueous or nonaqueous techniques. The oral dosage forms may be designed to release the active ingredient in a controlled manner, for example slow-release tablets or delayed-release tablets or capsules. Such controlled release dosage forms are particularly useful in cases where the therapeutically active compound has a short biological half-life, as is the case for the ester-containing compounds of this invention.

In addition to the common dosage forms set out above, the compounds of the present invention may also be administered by controlled release means and delivery devices such as those described in U.S. Pat. Nos. 3,845,770; 3,916,899; 3,536,809; 3,598,123; and 4,008,719, and PCT application WO92/20377, the disclosures of which are hereby incorporated by reference.

Pharmaceutical compositions of the present invention suitable for oral administration may be presented as discrete unit dosage forms such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally, with one or more accessory ingredients, as shown in Example 8.

Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding, in a suitable machine, a mixture of the powdered compound moistened with an inert liquid diluent. All of the foregoing techniques are well know to persons of skill in the pharmaceutical art. Each tablet may contain from about 0.1 mg to about 200 mg of the active ingredient.

The active ingredient is sieved through a suitable sieve and blended with the lactose until a uniform blend is formed. Suitable volumes of water are added and the powders are granulated. After drying, the granules are then screened and blended with the magnesium stearate. The resulting granules are then compressed into tablets of desired shape. Tablets of other strengths may be prepared by altering the fill weight and if necessary, changing the tablet weight to suit.

EXAMPLE 8

ORAL FORMULATION - TABLETS

| Ingredients | Quantity per tablet in mg | |
|---|---|---|
| | A | B |
| Active ingredient according to Example 2 (DIMEO) | 5.0 | 20.0 |
| Lactose BP | 148.5 | 133.5 |
| Starch BP | 30.0 | 30.0 |
| Pregelatinized Maize Starch BP | 15.0 | 15.0 |
| Magnesium stearate | 1.5 | 1.5 |
| Compression weight | 200.0 | 200.0 |

EXAMPLE 9

ORAL FORMULATION - CAPSULES

| Formula | Quantity per Capsule in mg. | |
|---|---|---|
| | A | B |
| Active ingredient according to Example 3 (DIHEO) | 5.0 | 20.0 |
| Starch 1500 | 94.5 | 79.5 |
| Magnesium Stearate BP | 1.0 | 1.0 |
| Compression Weight | 100.0 | 100.0 |

The active ingredient is sieved and blended with the excipients. The mixture is filled into suitably sized two-piece hard gelatin capsules using suitable machinery. Other doses may be prepared by altering the fill weight and if necessary, changing the capsule weight to suit.

We claim:
1. A compound represented by the following formula:

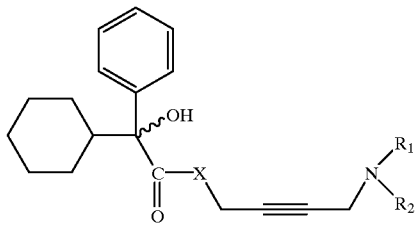

including stereochemically isomeric forms thereof and pharmaceutically acceptable salts thereof, wherein:

X is oxygen, —NH or methylene;

$R_1$ and $R_2$ are independently selected from the group consisting of: hydrogen, an alkyl group having 1 to 4 carbon atoms, $(CH_2)_2O$ and $(CH_2)_3OH$, with the proviso that:

(1) when X is oxygen:
  $R_1$ and $R_2$ are not both $CH_3$;
  $R_1$ and $R_2$ are not both $C_2H_5$;
  $R_1$ and $R_2$ are not both $C_3H_7$;
  $R_1$ and $R_2$ are not both $C_4H_9$;
  $R_1$ is not $C_2H_5$, when $R_2$ is hydrogen; and
  $R_1$ is not $CH_3$ when $R_2$ is $C_2H_5$;

(2) when X is —NH:
  $R_1$ is not hydrogen when $R_2$ is $CH_3$ when said compound is in the racemic form;
  $R_1$ is not hydrogen when $R_2$ is $C_2H_5$;
  $R_1$ and $R_2$ are not both $CH_3$;
  $R_1$ and $R_2$ are not both $C_2H_5$;
  $R_1$ and $R_2$ are not both $C_3H_7$;
  $R_1$ and $R_2$ are not both $C_4H_9$;
  $R_1$ is not $(CH_2)_2OH$ when $R_2$ is hydrogen or $CH_3$ or $C_2H_5$, when said compound is in the racemic form;
  $R_1$ is not $(CH_2)_3OH$ when $R_2$ is hydrogen or $CH_3$ or $C_2H_5$, when said compound is in the racemic form;

(3) when X is methylene:
  $R_1$ and $R_2$ are not both hydrogen when said compound is in the racemic form or in the R-form;
  $R_1$ and $R_2$ are not both $CH_3$ when said compound is in the racemic form or in the R-form;
  $R_1$ and $R_2$ are not both $C_2H_5$ when said compound is in the racemic form or in the R-form;
  $R_1$ is not hydrogen when $R_2$ is $CH_3$ when said compound is in the racemic form or in the R-form; and
  $R_1$ is not hydrogen when $R_2$ is $C_2H_5$ when said compound is in the racemic form or in the R-form.

2. An R-isomer of a compound of claim 1, substantially free of its S-isomer.

3. An S-isomer of a compound of claim 1, substantially free of its R-isomer.

4. A method for treating smooth muscle hyperactivity in a mammal, which comprises administering to said mammal a therapeutically effective amount of a compound of the formula:

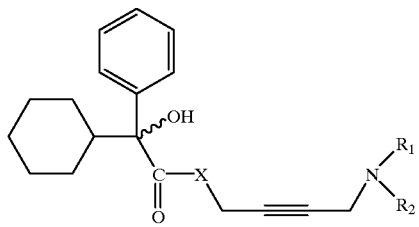

including stereochemically isomeric forms thereof and pharmaceutically acceptable salts thereof, wherein:

X is oxygen, —NH or methylene;

$R_1$ and $R_2$ are independently selected from the group consisting of: hydrogen, an alkyl group having 1 to 4 carbon atoms, $(CH_2)_2OH$ and $(CH_2)_3OH$, with the proviso that:

(1) when X is oxygen:
- $R_1$ and $R_2$ are not both hydrogen;
- $R_1$ is not hydrogen when $R_2$ is hydrogen, $CH_3$, $C_3H_7$ or $C_4H_9$, when said compound is in the racemic form or the R-form;
- $R_1$ is not $CH_3$ when $R_2$ is $CH_3$, $C_2H_5$, $C_3H_7$ or $C_4H_9$, when said compound is in the racemic form or the R-form;
- $R_1$ is not $C_2H_5$, when $R_2$ is $C_2H_5$, $C_3H_7$ or $C_4H_9$, when said compound is in the racemic form or the R-form;
- $R_1$ is not $C_3H_7$ when $R_2$ is $C_3H_7$ or $C_4H_9$, when said compound is in the racemic form or the R-form; and
- $R_1$ is not $C_4H_9$ when $R_2$ is $C_4H_9$, when said compound is in the racemic form or the R-form;

(2) when X is —NH:
- $R_1$ is not hydrogen when $R_2$ is hydrogen, $CH_3$, $C_2H_5$, $C_3H_7$ or $C_4H_9$ when said compound is in the racemic form or the R-form;
- $R_1$ is not $CH_3$ when $R_2$ is $CH_3$, $C_2H_5$, $C^3H_7$ or $C_4H_9$, when said compound is in the racemic form or the R-form;
- $R_1$ is not $C_2H_5$ when $R_2$ is $C_2H_5$, $C_3H_7$ or $C_4H_9$, when said compound is in the racemic form or the R-form;
- $R_1$ is not $C_3H_7$ when $R_2$ is $C_3H_7$ or $C_4H_9$, when said compound is in the racemic form or the R-form; and
- $R_1$ is not $C_4H_9$ when $R_2$ is $C_4H_9$, when said compound is in the racemic form or the R-form;

(3) when X is methylene:
- $R_1$ is not hydrogen when $R_2$ is hydrogen, $CH_3$, $C_2H_5$, $C_3H_7$ or $C_4H_9$ when said compound is in the racemic form or the R-form;
- $R_1$ is not $CH_3$ when $R_2$ is $CH_3$, $C_2H_5$, $C_3H_7$ or $C_4H_9$, when said compound is in the racemic form or the R-form;
- $R_1$ is not $C_2H_5$ when $R_2$ is $CH_2H_5$, $C_3H_7$ or $C_4H_9$, when said compound is in the racemic form or the R-form;
- $R_1$ is not $C_3H_7$ when $R_2$ is $C_3H_7$ or $C_4H_9$, when said compound is in the racemic form or the R-form; and
- $R_1$ is not $C_4H_9$ when $R_2$ is $C_4H_9$, when said compound is in the racemic form or the R-form.

5. The method of claim 4, wherein said smooth muscle hyperreactivity is the cause of urinary incontinence.

6. The method of claim 4, wherein said smooth muscle hyperreactivity is the cause of irritable bowel syndrome.

7. The method of claim 4, wherein said smooth muscle hyperreactivity is of non-muscarinic origin and said compound is an (S)-isomer, with no or minimal anti-cholinergic activity, substantially free of its corresponding (R)-isomer.

8. The method of claim 4, wherein said smooth muscle hyperreactivity is of muscarinic origin and said compound is an (R)-isomer, with anti-cholinergic activity, substantially free of its corresponding (S)-isomer.

9. The method of claim 4, wherein said compound or pharmaceutically acceptable salt thereof is administered in an amount of from 0.1 mg to about 200 mg, one to four times daily.

10. The method of claim 4, wherein said compound or pharmaceutically acceptable salt thereof is administered in an amount of from 0.3 mg to about 75 mg, one to four times daily.

11. The method of claim 4, wherein said compound or pharmaceutically acceptable salt thereof is administered by inhalation, parenterally, transdermally, ocularly, rectally or orally.

12. The method of claim 11, wherein said compound is administered orally.

13. A pharmaceutical composition comprising an (S)-isomer of a compound of claim 1 or a pharmaceutically acceptable salt thereof, substantially free of its corresponding (R)-isomer, and a pharmaceutically acceptable carrier.

14. The pharmaceutical composition of claim 13, wherein said compound comprises at least 98% by weight of said (S)-isomer.

15. A pharmaceutical composition comprising an (R)-isomer of a compound of claim 1 or a pharmaceutically acceptable salt thereof, substantially free of its corresponding (S)-isomer, and a pharmaceutically acceptable carrier.

16. The pharmaceutical composition of claim 13, wherein said compound comprises at least 98% by weight of said (S)-isomer.

17. A method for treating non-cholinergically mediated urinary incontinence in a mammal while reducing concomitant liability of adverse effects associated with the racemic mixture and the (R)-isomer, comprising administering to said mammal a therapeutically effective amount of the (S)-isomer set forth in claim 1 or a pharmaceutically acceptable salt thereof, substantially free of its (R)-isomer.

18. A method for treating cholinergically mediated urinary incontinence in a mammal while reducing concomitant liability of adverse effects associated with the racemic mixture and the (S)-isomer, comprising administering to said mammal a therapeutically effective amount of the (R)-isomer set forth in claim 1 or a pharmaceutically acceptable salt thereof, substantially free of its (S)-isomer.

19. A method for treating non-cholinergically mediated gastro-intestinal motility disorders in a mammal while reducing concomitant liability of adverse effects associated with the racemic mixture and the (R)-isomer, comprising administering to said mammal a therapeutically effective amount of the (S)-isomer set forth in claim 1 or a pharmaceuti-cally acceptable salt thereof, substantially free of its (R)-isomer.

20. A method for treating cholinergically mediated gastro-intestinal motility disorders in a mammal while reducing concomitant liability of adverse effects associated with the racemic mixture and the (S)-isomer, comprising administering to said mammal a therapeutically effective amount of the (R)-isomer set forth in claim 1 or a pharmaceutically acceptable salt thereof, substantially free of its (S)-isomer.

21. A method for treating non-cholinergically mediated dysmenorrhea in a mammal while reducing concomitant liability of adverse effects associated with the racemic mixture and the (R)-isomer, comprising administering to said mammal a therapeutically effective amount of the (S)-isomer set forth in claim 1 or a pharmaceutically acceptable salt thereof, substantially free of its (R)-isomer.

22. The method of claim 21, further comprising an analgesic or anti-inflammatory agent.

23. A method for treating cholinergically mediated dysmenorrhea in a mammal while reducing concomitant liability of adverse effects associated with the racemic mixture and the (S)-isomer, comprising administering to said mammal a therapeutically effective amount of the (R)-isomer set forth in claim 1 or a pharmaceutically acceptable salt thereof, substantially free of its (S)-isomer.

24. The method of claim 22, further comprising an analgesic or anti-inflammatory agent.

25. The method of claim 4, further comprising avoiding anticholinergic side effects.

26. The method of claim 4, further comprising avoiding arrhythmogenic side effects.

* * * * *